United States Patent [19]
Stüssi

[11] Patent Number: 5,913,242
[45] Date of Patent: Jun. 15, 1999

[54] PORTABLE JUMPING FORCE MEASURING PLATFORM

[75] Inventor: Edgar Stüssi, Spiegel, Switzerland

[73] Assignee: K.K. Holding AG, Winterthur, Switzerland

[21] Appl. No.: 09/089,386

[22] Filed: Jun. 3, 1998

[30] Foreign Application Priority Data

Jun. 4, 1997 [CH] Switzerland ............................ 1331/97

[51] Int. Cl.⁶ .................................................. A61B 5/22
[52] U.S. Cl. ........................ 73/379.04; 73/172; 73/865.4
[58] Field of Search ............ 73/379.01, 379.04, 73/862.541, 862.637, 172, 865.4; 600/587, 592

[56] References Cited

U.S. PATENT DOCUMENTS

| | | | |
|---|---|---|---|
| 3,504,540 | 4/1970 | Pradko et al. ........................ | 73/865.4 X |
| 3,894,437 | 7/1975 | Hagy et al. ............................ | 73/172 X |
| 4,136,682 | 1/1979 | Pedotti ................................... | 73/172 X |
| 4,928,959 | 5/1990 | Bassett et al. ..................... | 73/379.04 X |
| 5,029,483 | 7/1991 | Gautschi et al. ...................... | 73/172 X |
| 5,186,062 | 2/1993 | Roost ...................................... | 73/865.4 |
| 5,299,454 | 4/1994 | Fuglewicz et al. ........................ | 73/172 |
| 5,469,740 | 11/1995 | French et al. ..................... | 73/379.04 X |
| 5,574,669 | 11/1996 | Marshall ............................. | 73/865.4 X |

*Primary Examiner*—Elizabeth L. Dougherty
*Attorney, Agent, or Firm*—Barnes & Thornburg

[57] ABSTRACT

A measuring platform having three supporting units arranged in a triangle, fixed and fitted with force measuring sensors, and stabilized with each other via a baseplate so that it is also possible to measure simultaneous jump-off and/or landing forces for single and multiple jumps, regardless of the ground support.

16 Claims, 4 Drawing Sheets

PORTABLE JUMPING FORCE MEASURING PLATFORM

BACKGROUND AND SUMMARY OF THE INVENTION

When training for many forms of sport, the jumping force of the leg muscles plays a decisive role. Accordingly there is a need to be able to measure primarily the jumping-off force in single and multiple jumps, and secondarily the landing or rebound force and the flight time between both measuring points.

Contact mats measuring the flight time by inbuilt surface contacts are state of the art, but they allow only certain conclusions about the jump-off force without yielding the exact values. The advantage of these mats lies in their low price and simple laying and transportation. Their chief disadvantage is that the jump-off force, its behaviour versus time at the conversion into the jump, and the cushioning of the landing, remain unknown. This essential features of training results are not discernable. Thus, application of jumping mats is restricted.

These disadvantages are to be overcome by the jumping force measuring platform according to the invention. This platform is also portable, and may be placed on any hard surface. The jumping force is determined statically by three fixed supporting units, enabling exact measuring of the forces acting on it because force measuring sensors are integrated in the supporting units. Thus for the first time there is a measuring platform enabling the forces involved in jumping to be measured in absolute values. Above all, in multiple jumps for example, the complete force curve from landing to rebound can be measured and analyzed in one jump phase.

For the training sportsman, a triangular platform is not very efficacious in itself. Within the scope of the invention, however, it can be extended into a rectangle with a further supporting unit, which may be fitted likewise with a force measuring sensor. It is also possible to extend the triangular form into an approximate or true circle or polygon with articulating elements, without altering the results obtained with the triangular configuration.

Baseplate and articulating elements can be assembled or collapsed, giving a package of reduced geometric dimensions in the collapsed state. At the place of use for force measuring, the package is opened and assembled appropriately, providing an enlarged measuring surface which is also easily perceptible to the jumper, enabling him to work on the centroid of the surface.

Baseplates and articulating elements in triangular configuration are advantageously joined to each other so that the swivel axis is as close as possible to the line joining two neighbouring force measuring sensors. These should be disposed so that they are immediately close to a swivel axis. In the immediate proximity of a swivel axis, only two force sensors are needed.

By using triangular assemblies and placing the supporting units in the corners of the triangles or their immediate vicinity, a stable plate support unlikely to tilt is obtained.

It is advantageous to join articulating elements having preferably only one supporting unit with a baseplate, so that their supporting unit is not close to the baseplate.

The invention thus provides a metrologically simple and exact arrangement with at least doubled jumping surface, without any accident risk and easily transportable. The invention also enables the principal parameters to be combined in one construction form:

Exact measuring of jump data, especially the force curve upon landing and rebounding in multiple jumps.

Easy visual perception of the platform by the trainee, without accident risk.

Simple transportation and setting-up.

Low-cost and dependable platform design. Other objects, advantages and novel features of the present invention will become apparent from the following detailed description of the invention when considered in conjunction with the accompanying drawings.

BRIEF DESCRIPTION OF THE DRAWINGS

The ideas embodied in the invention will be explained in more detail with reference to the figures.

DETAILED DESCRIPTION OF THE PREFERRED

In its basic embodiment the measuring platform rests on a floor 1 (FIG. 1) as hard as possible through three supporting units 2 arranged in the form of a triangle. These are joined with each other through the baseplate 3 and mutually stabilized, so that the supporting units 2 may be arranged in any triangle actually, though an equilateral or right-angled triangle is preferable, as is made clear in FIG. 5.

Figure 1:
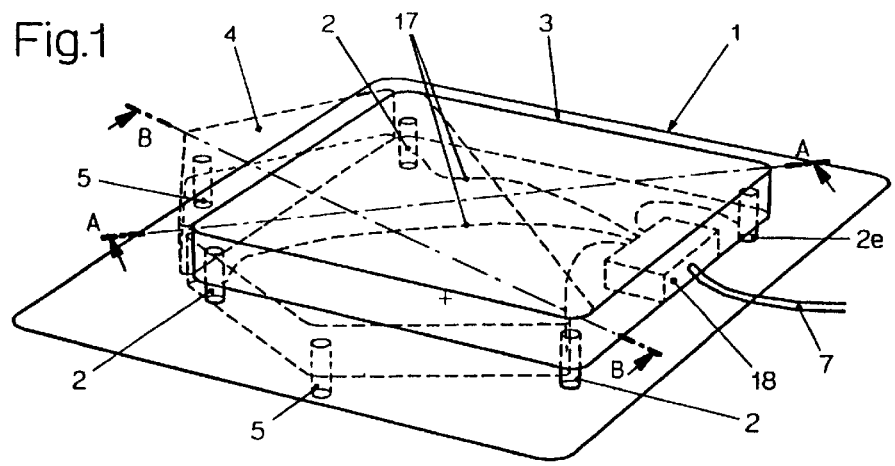
FIG. 1 Perspective view of the platform according to the invention with articulated elements shown with broken lines.

In FIG. 1 the baseplate 3 is represented with solid lines extended into a rectangle — the triangular form is indicated with broken lines — and supported on the floor 1 through an additional supporting unit 2e, which may be made adjustable in height. The supporting units 2, 2e of the baseplate 3 are generally fitted with force measuring sensors 6 (FIG. 7), the particular measuring signal being led via cable 17 to a collecting point 18, which has an amplifier and is integrated in the baseplate 3. Here it is interconnected or led out as an individual signal to data processing, which is effected by known methods and will not be dealt with further, as the invention is concentrated on the plate configuration.

Figure 5:
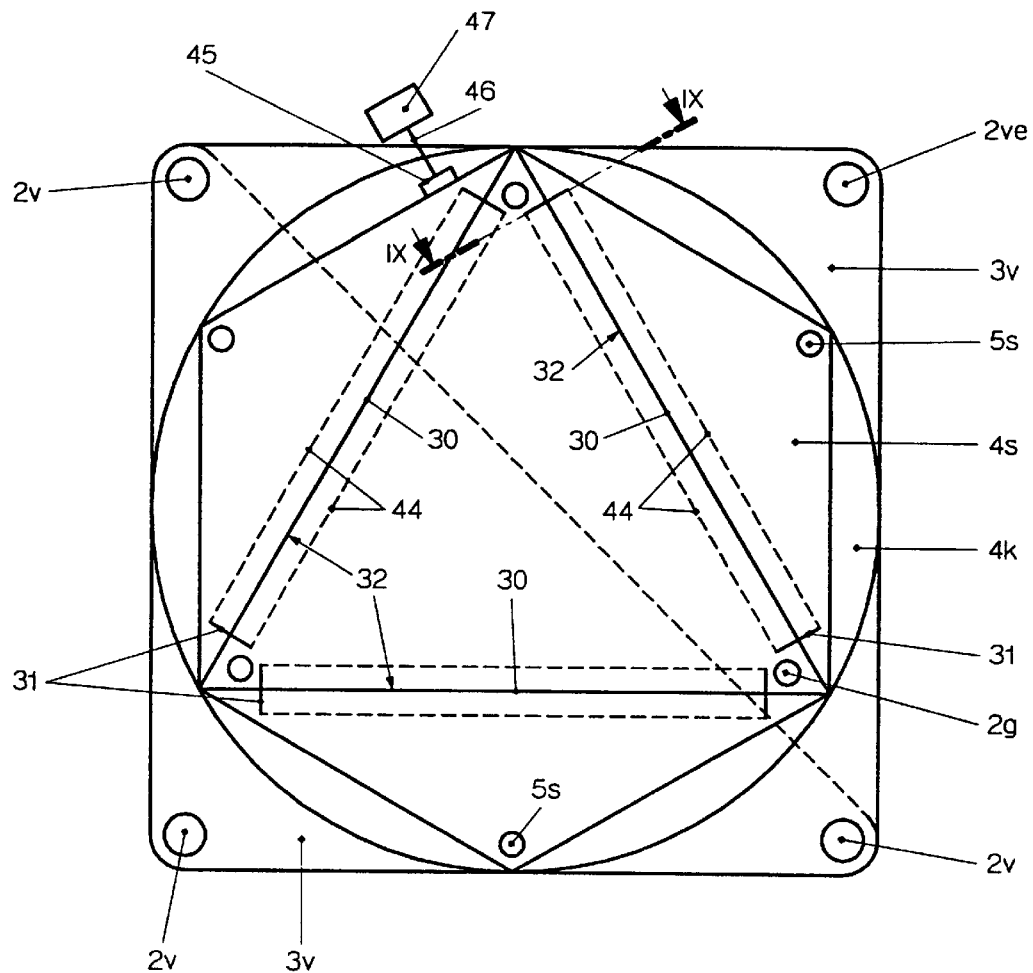
FIG. 5 Various possible embodiments of the new measuring platform shown in plan, all superimposed.

As a variant of the rectangular extension, FIG. 1 shows with broken lines, articulating elements 4 attachable to the triangle sides of the baseplate 3, which may also be used to extend the triangular baseplate 3. As shown in FIG. 5 they are used preferably in conjunction with a basic equilateral triangle form, forming a base surface as obtuse-angled triangles or circle segments (FIG. 5) for example. They are supported on the floor 1 through supporting units 5, which lie removed from the baseplate 3 and are mostly not provided with sensor elements 6.

Figure 2:
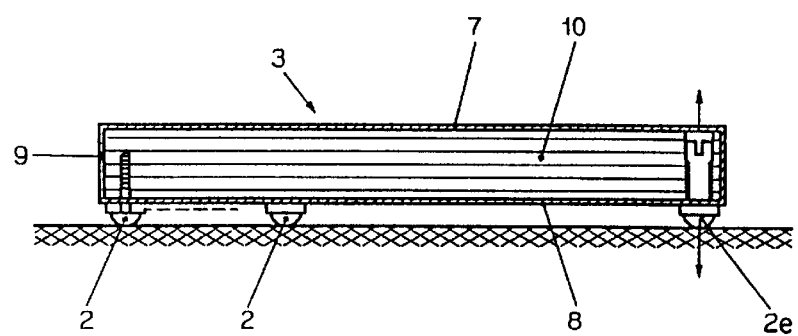
FIG. 2 Section through platform along line A—A of FIG. 1.

Above all, the greatest possible stiffness is required in the baseplate 3, so that its natural frequency is clearly above 100 Hz. An optimum of minimal weight and maximal stiffness can be achieved with honeycomb structures, as have been employed in space travel. Low-cost approximations are light alloy plates with lightweight filling materials as interlayers, in sandwich construction, for example. A top plate 7 (FIG. 2), a bottom plate 8 and a surrounding wall 9 may be combined typically to give a hollow body of aluminium alloy, for example which is filled with material 10 pressed or poured in. Suitable also are wooden or plastic plates. The articulating elements 4 may consist similarly of a sheet metal casing packed with filling material.

Figure 3:
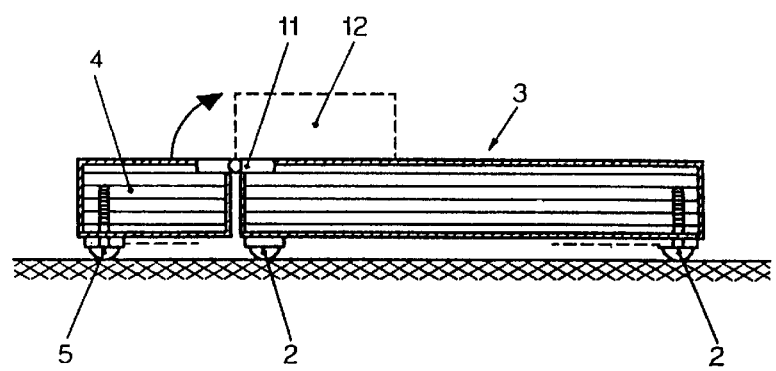
FIG. 3 Section through platform along line B—B of FIG. 1, with articulating element hinging up.

FIG. 3 shows a baseplate 3 in the form of an equilateral triangle to which an articulating element 4 is joined, attached to the baseplate with the hinge 11. This enables it to be hinged over for transportation. This presupposes that the articulating element 4 measuring is not more than a third of the base plate 3, i.e. forming an obtuse-angled isosceles triangle.

Figure 4:
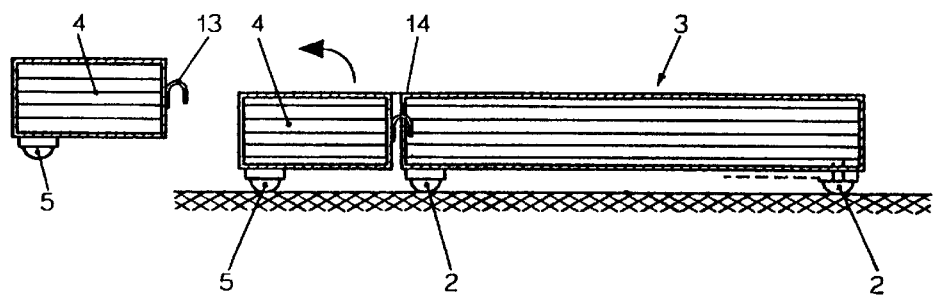
FIG. 4 Another embodiment with attachable articulating element shown as in FIG. 3.

FIG. 4 shows an articulating element 4 attached in a coupler opening 14 and coupled by means of a coupling element 13 to the unilaterally triangular baseplate 3 in turn. This variant allows simple detachment of the articulating elements 4 for transportation. At the same time its shape is less restricted, so that it may be take the form of a circle segment.

FIG. 5 shows once more the relatively simple examples described previously of various embodiments of the new measuring platform, all three variants being shown here with a common center.

One baseplate 3v which, as shown by the broken hypotenuse, has the form of a right-angled triangle with the supporting units 2v joined together and is extended into a rectangular platform with the additional supporting unit 2ve. One possibility for ensuring a statically stable support for this is to make the adjustable supporting unit 2ve adjustable in height. Though the baseplate 3v is shown only as a single integral plate, it can of course be divided into two right-angled triangles along the broken hypotenuse. Like the designs shown in FIGS. 3 and 4, the two triangles may be joined by hinges or coupling links to form the rectangular platform.

Attached to the equilateral triangular baseplate 3g, which rests on supporting units 2g, are either obtuse-angled articulating elements 4s or segmental articulating elements 4k along all three sides. Each articulating unit resting on a supporting unit 5s, which may be fitted with a sensor 6 or not.

Needless to say, for the baseplate 3 and/or the articulating elements 4 other triangular forms may be adopted too, such as oblique-angled, rectangular or polygonal forms. However, the triangular forms shown permit a closed measuring surface to be obtained in particularly simple fashion.

Figure 6:
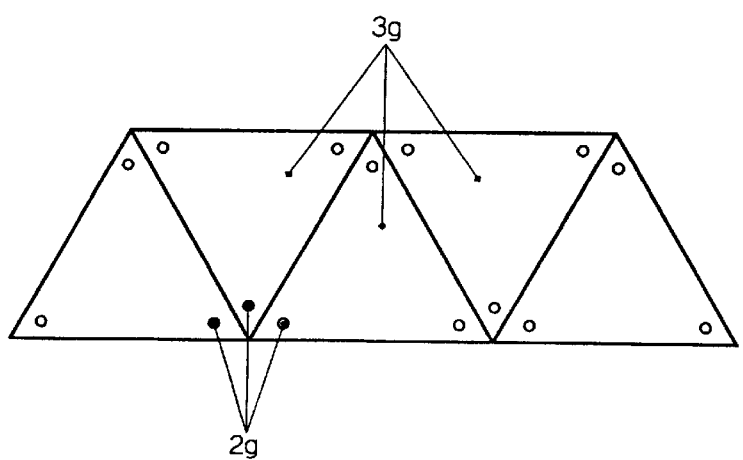
FIG. 6 Several measuring platforms with baseplates in the form of equilateral triangles joined to form a jump-off/landing measuring facility.

In FIG. 6 five equilateral triangular baseplates 3g are combined into a measuring strip, enabling measurement during multiple jumps like the hop, skip and jump in light athletics, registering the first jump, the first landing, the next jump, the second landing, a third jump and possibly a third landing. Of course an assembly of this kind is not confined to a single track but may assume other surface configurations also.

Figure 8:
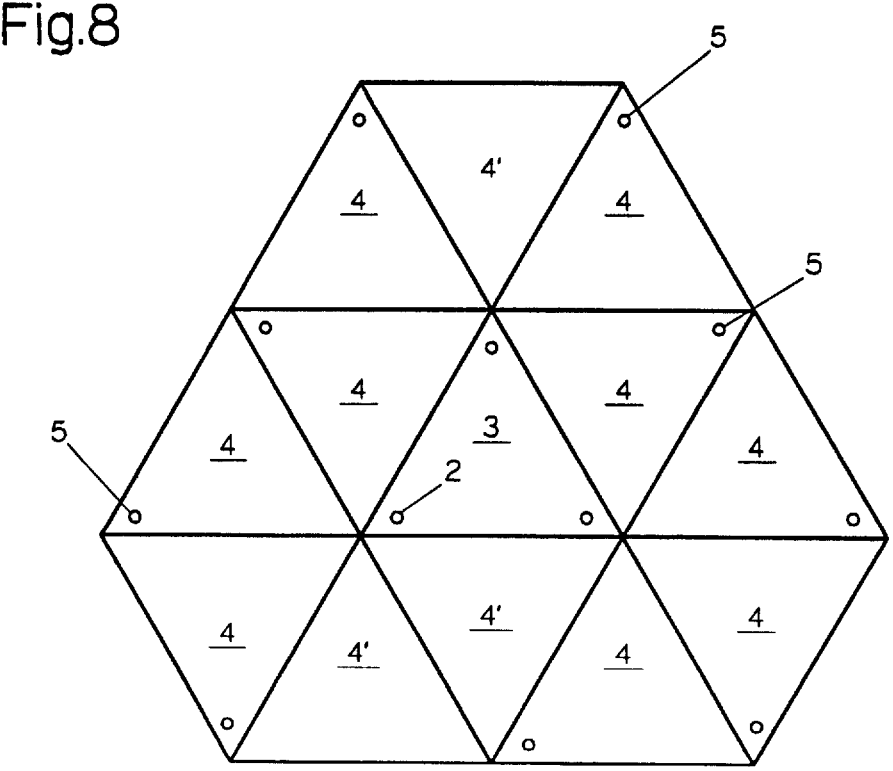
FIG. 8 Polygonal surface assembly comprising a number of triangular elements.

Thus FIG. 8 shows a polygonal measuring surface assembled from basic elements in the form of equilateral triangles. Besides at least one baseplate 3 having supporting elements 2 fitted with sensors, articulating elements 4 of the same area as the baseplate 3 are provided. In this case these articulating elements can be fitted to advantage with supporting units 5 having sensors, or else lacking these (articulating elements 4') as long as there are two sensor-fitted supporting units 2 or 5 in the immediate proximity of a connection of two elements. Of course it is also possible to assemble a polygonal measuring surface from baseplates 3 alone.

Figure 7:
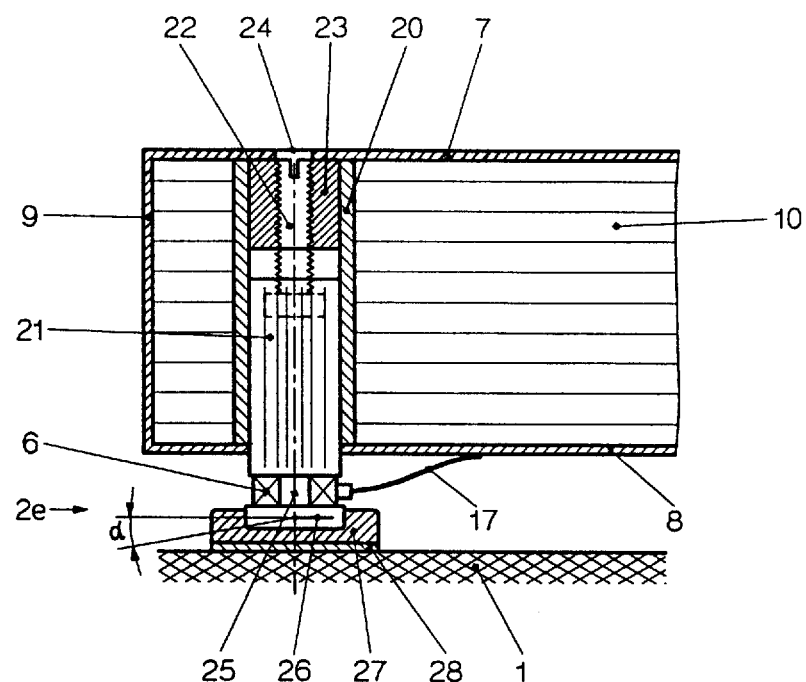
FIG. 7 Adjustable supporting unit in section A—A of FIG. 1 shown in detail.

In the example of an embodiment of a supporting element 2 or 5 according to FIG. 7, welded into the sheet metal casing 7–9 of a baseplate 3 or an articulating element 4 is a sleeve 20, into which a cylinder 21 is inserted. Its upper face is engaged by an adjusting screw 22 with supporting unit 2e adjustable in height. This screw is guided in a threaded bush 23 fixed in the sleeve 20 and is accessible through an opening 24 in the top plate 7 for adjusting.

Screwed into the cylinder 21 from below is another screw 25 with a flat, disk-shaped head 26, through which the sensor 6 is forced against the cylinder 21, possibly under preload. Its head 26 rests in a bearing shell 27, which in turn rests on the ground 1 through an elastic interlay 28. Due to its compressibility this allows a certain "height alteration", and also swivelling motions about the mid-point of the screw head 26 (angle α). In this way, in conjunction with or instead of the height adjustability a statically stable support is obtained, with a rectangular platform for example.

Supporting units 2 or 5 without height adjustment can also be constructed in the manner described above. With these the adjusting screw 22 is merely fixed unreleasable. Supporting units 5 lacking sensors have the sensor 6 replaced by a correspondingly dimensioned spacer.

Figure 9:
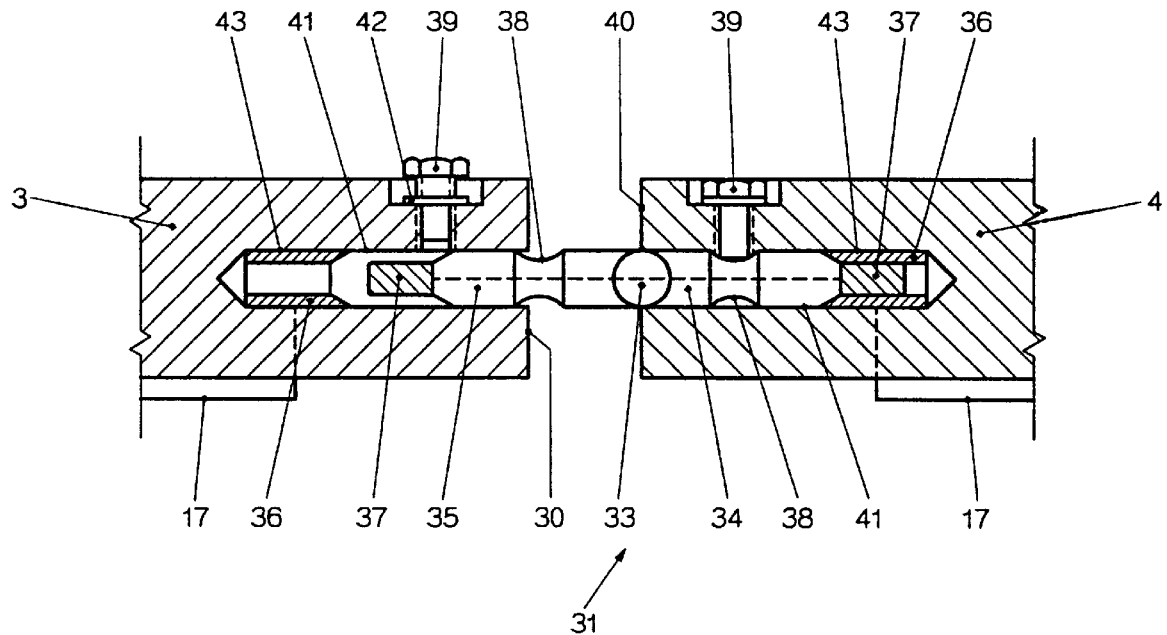
FIG. 9 Cross section along the line IX—IX in FIG. 5, showing a connection between the baseplate and an articulating element of the measuring plate according to the invention.

A baseplate 3 and the articulating elements 31 arranged swivellable on its edges or faces 30 (FIG. 5) as the case may be are linked by the joint elements 31 shown in cross section in FIG. 9. There are two joint elements 31 for each swivel axis 32 (FIG. 5). The joint elements 31 are placed in the corners of the baseplate 3 and the articulating elements 4. The spacing of the corners of the baseplate 3 and of the corners of the articulating elements 4 is governed solely by the material thickness necessary for inserting the joint elements 31. The positions of the joint elements 31 are indicated by broken lines in FIG. 5.

The joint elements 31 as shown in FIG. 9 have a hinge joint 33 with a pin 34 and 35 at each side. Pin 35 is shown not entered completely, to enable the two plug parts 36 and 37 of the floating socket connection described below to be shown schematically. The pins 34 and 35 have a round or angular cross section and a circumferential groove 38 adjacent their free end. Engaging each groove 38 from the surface of the baseplate 3 or from an articulating element 4 is a fixing screw 39, with which each pin can be secured against rotating. In the faces 30 and 40 are the blind holes 41 matching the pins 34 and 35. The screw shank length is chosen so that the top of the screw head is flush with the particular surface when screw 39 is screwed in, so that no sportsman can get caught on the screw head or stumble over it in use for instance. Under each screw head is a spring lock washer 42 to prevent it unscrewing on its own.

The circular cross sections of pins 34 and 35 were selected only on account of better producibility. Rotation is prevented here only by the clamping force of the screws 39. It would, however, be better to have a positive prevention of rotation between the pins and matching openings instead of the blind holes. For example a triangular, square or rectangular cross section with corresponding pin cross section might be adopted. Pin and opening would be formed with a close clearance fit. Unlike the blind hole 41 mentioned, with its circular cross section which can be machined with a single drilling, non-circular openings would be less easy to machine, calling typically for an internal broach. Non-circular blind holes might also be produced by milling, if the milled groove were subsequently covered with a plate. If the pin were turned in its opening so much that the axis of the hinge joint 33 were no longer parallel with the intersection line of parallel planes to the surfaces of the baseplate 3 and the corresponding articulating element 4 namely, force would be taken up in the corresponding hinge joint, so that the measured result described below would be falsified.

In the bottom of each blind hole 41 is a floating first plug part 36. A matching second plug part 37 is provided at the end of each pin 34 and 35. Various designs may be adopted for the floating assembly. The plugs 36 and 37 may be bedded in soft rubber for example, and one of the plug parts, in this case 36 for instance, might be provided with an entering cone 43. All force sensors 6 are linked via their energy supply and signal cables 17 with all plug parts 35, i.e. all plug parts 36 of a unit are looped together with regard to energy and signals via cables 44 shown with broken lines in FIG. 5. Into one of the blind holes still free, a plug 45 provided with a hand grip is inserted having a plug part analogous to plug part 37. Plug 45 is then connected with energy supply and evaluation electronics 47 via cable 46. Each of the force measuring sensors 6 has an electronic code, by which the electronics 47 can recognize each force measuring sensor 6 and query its measured values for processing. As the positions of the sensors 6 are known in each unit 3 and 4, the force acting on the unit, its behaviour versus time and its point of action can be determined from the level of the measuring signal.

Figure 10:
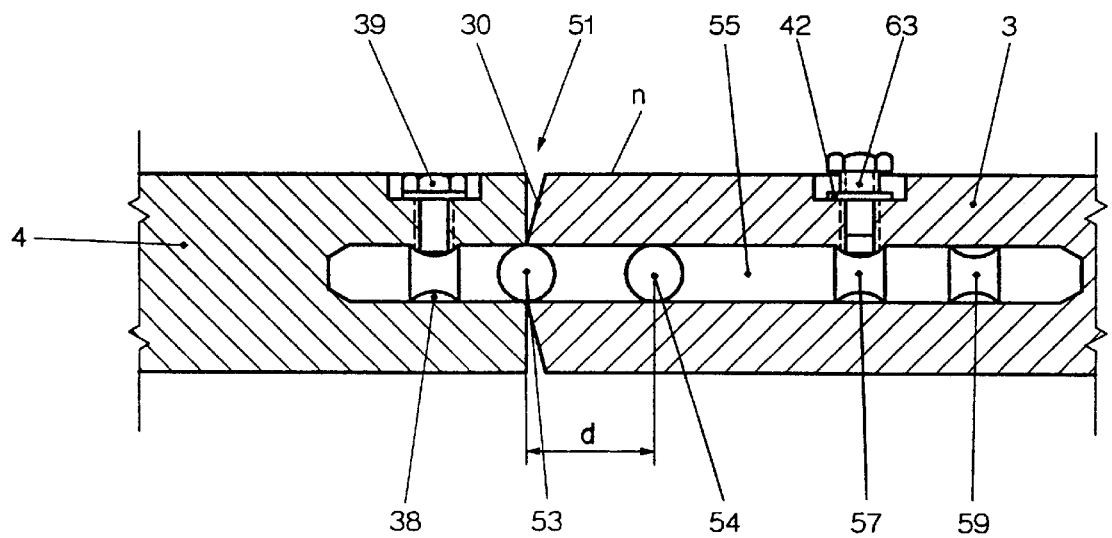
FIG. 10 A variant of the connection between baseplate and articulating element shown in FIG. 9.

Instead of constructing the measuring platform according to the invention, dismantlable of baseplate and articulating elements, it can be built with the articulating elements 4 folding onto the top of the baseplate 3. To enable the articulating elements 4 to fold in and out, the joint element 31 is modified as shown in FIG. 10 for example. Unlike the one in FIG. 9, the joint element 51 shown in FIG. 10 has two hinge joints 53 and 54. The pin 55, insertable in the baseplate 3 for example, has unlike pin 55 two circumferential grooves 57 and 59 at some distance apart. The other pin 61 is analogous in form to pin 34. The plug parts for the energy supply and signal transmission are analogous to those of joint element 31 and are not shown here. If the articulating elements are to be folded over the baseplate, the screws 63 are unfastened in bedplate 3 and pin 55 is withdrawn till the hinge joint 54 lies at the location of hinge joint 53 shown in FIG. 10. Hinge link 53 then lies before the face 30 of the bedplate 3 at a distance d, which exceeds by a tolerance twice the distance of the pin axis from the surfaces n of the bedplate and the articulating element. Strictly speaking, the distance d ought to equal the sum of the distance from the axis of pin 61 to the surface of articulating element 4 plus the distance from the axis of pin 55 to the surface of the baseplate 3, but since the two surfaces are as one as a rule, the simplification set out above may be employed.

Although the present invention has been described and illustrated in detail, it is to be clearly understood that the same is by way of illustration and example only, and is not to be taken by way of limitation. The spirit and scope of the present invention are to be limited only by the terms of the appended claims.

I claim:

1. A measuring platform for sports training comprising:
   a base plate having at least three sides and a top surface;
   at least three supporting units arranged in a triangle, being stabilized in relation to each other by the baseplate, and supporting the baseplate on a ground surface;
   a force measuring sensor coupled to each supporting unit so that the forces involved in jumping up and/or landing on the top surface can be measured exactly and simultaneously, for single and multiple jumps, regardless of the ground surface; and
   one or more additional elements having a top surface and a supporting unit and beings adjustable joined to a side of the baseplate to extend the total top surface of the platform.

2. A measuring platform according to claim 1, wherein the supporting units of the additional elements includes a sensor.

3. A measuring platform according to claim 1, wherein the additional elements form obtuse-angled triangles and are linked to the baseplate by hinges so that the obtuse-angled triangles can be hinged over for transportation.

4. A measuring platform according to claim 1, wherein the additional elements are joined to the baseplate by a joint link and coupler opening so that they may be removed for transportation.

5. A measuring platform according to claim 1, wherein the additional elements are provided with supporting units which are not fitted with sensors and are dimensioned so that they have the same overall height as the supporting units fitted with sensors.

6. A measuring platform according to claim 5, wherein the supporting units of the additional elements are likewise fitted with sensors.

7. A measuring platform according to claim 1, wherein the supporting units are supported on the ground by elastic inlays.

8. A measuring platform according to claim 1, wherein the baseplate is a lightweight construction and has a natural frequency of at least 100 Hz.

9. A measuring platform according to claim 1, including joint elements with a joint head capable of turning about an axis without play, to which an insertable flange is arranged at both sides, and each corner of the baseplate faces and the coupling faces of each additional element having insertion cavities, into which the insertable flange can be fitted to join the baseplate to the corresponding additional element.

10. A measuring platform according to claim 9, including a releasable clamping device which secures each insertable flange in its cavity against slipping out.

11. A measuring platform according to claim 1, including floating, detachable plugs for transmitting electrical energy and signals between the individual force measuring sensors of the baseplate and possibly the additional elements.

12. A measuring platform according to claim 1, wherein the baseplate and an additional element extends the total top surface of the platform into a rectangle.

13. A measuring platform according to claim 1, wherein the baseplate and additional elements form a circle-like top surface of the platform.

14. A measuring platform for sports training comprising:
- a base plate having a top surface on a honeycomb structure;
- at least three supporting units being stabilized in relation to each other by the baseplate and supporting the baseplate on a ground surface; and
- a force measuring sensor coupled to each supporting unit so that the forces involved in jumping up and/or landing on the top surface can be measured exactly and simultaneously, for single and multiple jumps, regardless of the ground surface.

15. A measuring platform according to claim 14, wherein the baseplate is of a lightweight construction and has a natural frequency of at least 100 Hz.

16. A measuring platform for sports training comprising:
- a base plate having a top surface being of a lightweight construction and having a natural frequency of at least 100 Hz;
- at least three supporting units being stabilized in relation to each other by the baseplate and supporting the baseplate on a ground surface; and
- a force measuring sensor coupled to each supporting unit so that the forces involved in jumping up and/or landing on the top surface can be measured exactly and simultaneously, for single and multiple jumps, regardless of the ground surface.

* * * * *